United States Patent [19]

Pascal

[11] Patent Number: 4,713,382
[45] Date of Patent: Dec. 15, 1987

[54] N-PHENYL-4-PHENYL-1-PIPERAZINECAR-BOXAMIDINES AND RELATED COMPOUNDS AS ANTIARRHYTHMIC AGENTS

[75] Inventor: Jean-Claude Pascal, Cachan, France

[73] Assignee: Syntex (U.S.A.) Inc., Palo Alto, Calif.

[21] Appl. No.: 739,393

[22] Filed: May 30, 1985

[51] Int. Cl.[4] .................. A61K 31/495; C07D 295/06; C07D 295/12

[52] U.S. Cl. .................................. 514/255; 544/392; 544/393

[58] Field of Search ................ 544/392, 393; 514/255

[56] References Cited

U.S. PATENT DOCUMENTS

| | | | |
|---|---|---|---|
| 3,655,667 | 4/1972 | Kaiser et al. | 544/392 |
| 3,793,322 | 2/1974 | Shroff et al. | 544/389 |
| 3,961,056 | 6/1976 | Ducharme | 514/255 |
| 3,976,643 | 8/1976 | Diamond et al. | 544/159 |
| 4,211,867 | 7/1980 | Rasmussen | 544/60 |
| 4,259,334 | 3/1981 | Pascal | 544/391 |
| 4,374,835 | 2/1983 | Favier et al. | |

FOREIGN PATENT DOCUMENTS

| | | |
|---|---|---|
| 574981 | 10/1957 | Canada . |
| 641172 | 2/1984 | Switzerland . |
| 948766 | 2/1964 | United Kingdom . |
| 1514907 | 6/1978 | United Kingdom . |
| 1514198 | 6/1978 | United Kingdom . |
| 2057441 | 4/1981 | United Kingdom . |

OTHER PUBLICATIONS

Demler et al., Chem. Abst. vol. 95, 1981, 4263d eq. UK '442.

Primary Examiner—Donald G. Daus
Assistant Examiner—Cecilia Shen
Attorney, Agent, or Firm—Ellen J. Wise; Tom M. Moran; Brian Lewis

[57] ABSTRACT

Compounds having the formula

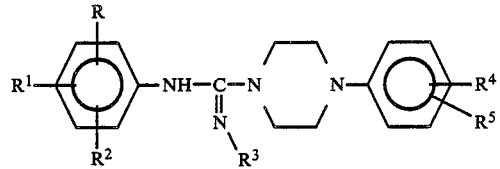

wherein R, $R^1$, $R^2$, $R^3$, $R^4$ and $R^5$ have the definitions given herein, are useful as antiarrhythmic agents.

20 Claims, No Drawings

N-PHENYL-4-PHENYL-1-PIPERAZINECARBOX-AMIDINES AND RELATED COMPOUNDS AS ANTIARRHYTHMIC AGENTS

BACKGROUND OF THE INVENTION

1. Field of the Invention

This invention relates to (i) novel N-phenyl-4-phenyl-1-piperazinecarboxamidines and the pharmaceutically acceptable acid addition salts and esters thereof, (ii) pharmaceutical compositions comprising a compound of this invention and at least one pharmaceutically acceptable excipient, (iii) the use of these compounds as antiarrhythmic agents in mammals; and (iv) processes for preparing the compounds of this invention.

2. Related Art

The compounds of this invention are N-phenyl-4-phenyl-1-piperazinecarboxamidines. Somewhat structurally related compounds are disclosed in U.S. Pat. No. 4,211,867, which describes 1-N-phenyl-pyrollidinecarboximidamides. In U.K. Patent Application No. GB 2,057,441, N-(trimethoxybenzyl)-piperazines are disclosed to have stimulatory action on mammalian circulation. U.S. Pat. No. 4,259,334 discloses piperazinemethanimine derivatives possessing useful antiarrhythmic properties. U.S. Pat. No. 3,793,322 discloses $N^1$-(phenyl)-$N^4$-(N-alkyliminobenzyl)piperazines as antihypoglycemic agents.

SUMMARY

This invention relates to novel N-phenyl-4-phenyl-1-piperazinecarboxamidines represented by the formula:

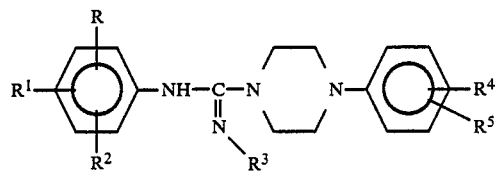
(I)

in which:

R, $R^1$ and $R^2$ are each independently hydrogen, halo, lower alkyl, lower alkoxy, —$CF_3$ or —$NO_2$;

$R^3$ is hydrogen, lower alkyl, lower alkyl—OH,

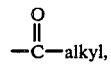

or lower alkenyl; and $R^4$ and $R^5$ are each independently hydrogen, halo, lower alkoxy, —OH, —$CH_3$ or

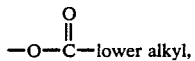

and the pharmaceutically acceptable acid addition salts and esters thereof.

In a second aspect, this invention relates to a pharmaceutical composition comprising a compound of Formula I and at least one pharmaceutically acceptable excipient.

A third aspect of the invention concerns methods of using compounds of Formula I, or pharmaceutical compositions thereof, as antiarrhythmic agents in mammals.

A fourth aspect of the invention concerns processes for the preparation of compounds of Formula I.

DETAILED DESCRIPTION OF THE INVENTION

Definitions:

"Lower alkyl" means a branched or unbranched hydrocarbon chain containing 1 to 4 carbon atoms, including, but not limited to, methyl, ethyl, n-propyl, isopropyl, n-butyl, sec-butyl, isobutyl, and the like. Of these, methyl and ethyl are preferred.

"Alkyl" means a branched or unbranched hydrocarbon chain containing 1 to 8 carbon atoms, thus including, but not limited to methyl, ethyl, n-propyl, isopropyl, n-butyl, sec-butyl, isobutyl, tert-butyl, isohexyl, n-heptyl, n-pentyl, tert-pentyl, 5-methylhexyl, isoooctyl, n-octyl, and the like. Of these, hydrocarbon chains of 1 to 4 carbon atoms are preferred.

"Lower alkoxy" means the group -O-lower alkyl where lower alkyl has the definition given above. Methoxy and ethoxy are preferred.

"Lower alkenyl" means a branched or unbranched unsaturated hydrocarbon chain of 2 to 4 carbon atoms, including ethylene, propylene, 1-butene, 2-butene, isobutylene and the like. A preferred alkenyl group is $CH_2$—CH=$CH_2$.

"Alkanoyl" refers to the group

wherein alkyl has the definition given above.

"Halo" refers to the halogen radicals bromo, chloro, fluoro and iodo. Chloro is a preferred halo-substituent.

"Mammals" refers to humans as well as all other mammalian species, including dogs, cats, horses, cattle, pigs, etc.

"Pharmaceutically acceptable acid addition salts and esters" refers to those salts and esters which retain the biological effectiveness and properties of the free bases and which are not biologically or otherwise undesirable. The acid addition salts are formed with inorganic acids such as hydrochloric acid, hydrobromic acid, sulfuric acid, nitric acid, phosphoric acid and the like, and organic acids such as acetic acid, lactic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid, ascorbic acid and the like. The pharmaceutically acceptable esters are prepared from the compounds of Formula I by reaction with an acid halide or anhydride corresponding to the desired ester, e.g. a 1 to 8 carbon branched or straight chain alkanoyl halide or anhydride. Typical alkyl ester groups are, for example, methyl, ethyl, propyl, isopropyl, butyl, t-butyl, isoamyl, pentyl, isopentyl, hexyl, isooctyl and the like.

The compounds of this invention are named as N-phenyl-4-phenyl-1-piperazinecarboxamidines using the numbering system set forth below:

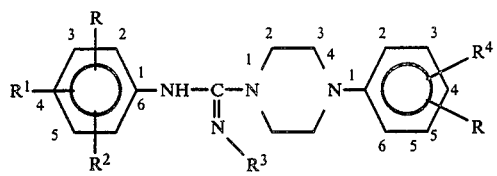

For example, the compound of Formula I where R, $R^3$ and $R^5$ are hydrogen, $R^1$ and $R^2$ are both chloro in the 3- and 5- positions, and $R^4$ is methoxy in the 2-position, is named N-[3,5-dichlorophenyl]-4-[2-methoxyphenyl]-1-piperazinecarboxamidine. The dimethane sulfonic acid salt of this compound is named as the dimethane sulfonate, i.e., 1-piperazinecarboxamidine N-[3,5-dichlorophenyl]-4-[2-methoxyphenyl], dimethane sulfonate.

Preferred Compounds

One preferred subclass of compounds of the invention includes compounds of Formula I in which R is hydrogen. Of these, a particularly preferred group are those Of these, a particularly preferred group are those wherein $R^4$ and $R^5$ are each independently hydrogen, —OH or lower alkoxy and at least one of $R^4$ and $R^5$ is not hydrogen. Within this group, of particular interest are compounds in which $R^4$ and $R^5$ are each independently hydrogen, —OH or lower alkoxy in the 2- and 4- positions of the phenyl ring, and $R^3$ is hydrogen, lower alkyl or lower alkyl—OH.

Another preferred subclass of compounds includes compounds of Formula I in which R is hydrogen, $R^1$ and $R^2$ are each independently hydrogen, lower alkyl, or halo, and at least one of $R^1$ and $R^2$ is not hydrogen. Within this subclass, a preferred group are compounds in which $R^4$ and $R^5$ are each independently hydrogen, —OH or lower alkoxy, and at least one of $R^4$ and $R^5$ is not hydrogen. Among these, a particularly preferred subgroup includes compounds in which $R^4$ and $R^5$ are each independently hydrogen, —OH or lower alkyl in 2- and 4- positions and $R^3$ is hydrogen, lower alkyl or lower alkyl—OH. Of these, especially preferred are compounds of Formula I in which $R^1$ and $R^2$ are each independently hydrogen, methyl or chloro.

At the present time, the most preferred compounds of this invention are:

N-[3,5-dichlorophenyl]-4-[2-methoxy-4-hydroxyphenyl]-1-piperazinecarboxamidine;

N-[3,5-dichlorophenyl]-4-[2-methoxyphenyl]-1-piperazinecarboxamidine;

N-[3,4-dichlorophenyl]-4-[2-methoxyphenyl]-1-piperazinecarboxamidine;

N-[3,4-dichlorophenyl]-N'-[isobutyl]-4-[2-methoxyphenyl]-1-piperazinecarboxamidine;

N-[phenyl]-N'-[3-hydroxypropyl]-4-[2-methoxyphenyl]-1-piperazinecarboxamidine, and the pharmaceutically acceptable acid addition salts and esters thereof.

Also of interest are:

N-[3,5-dichlorophenyl]-4-[4-fluorophenyl]-1-piperazine carboxamidine;

N-[3,5-dichlorophenyl]-4-[3-trifluoromethylphenyl]-1-piperazinecarboxamidine;

N-[phenyl]-N'-[isobutyl]-4-[2-methoxyphenyl]-1-piperazinecarboxamidine, and

N-[phenyl]-N'-[n-butyl]-4-[2-methoxyphenyl]-1-piperazinecarboxamidine, and the pharmaceutically acceptable acid addition salts thereof.

METHODS OF PREPARATION

A. Compounds of Formula I in which $R_3$ is hydrogen

Compounds of the invention in which $R_3$ is hydrogen can be prepared as shown in Reaction Scheme I, below:

REACTION SCHEME I

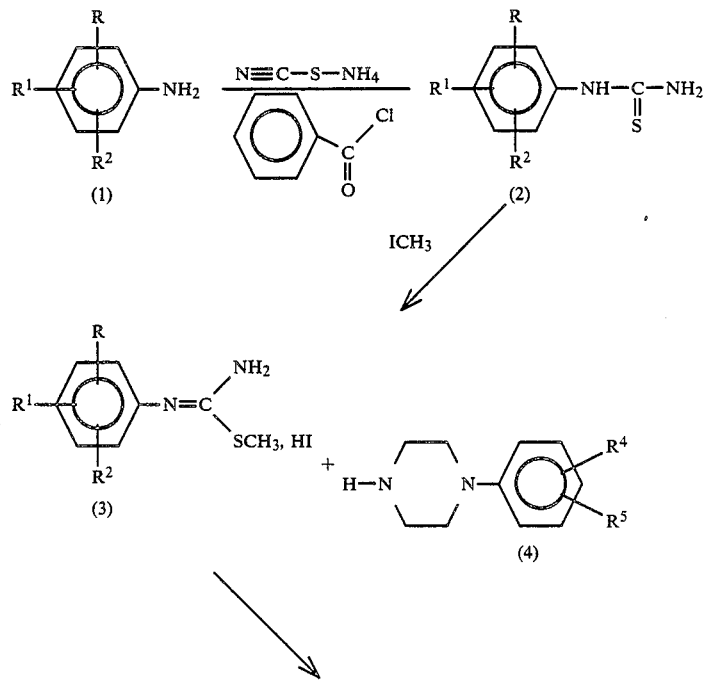

REACTION SCHEME I

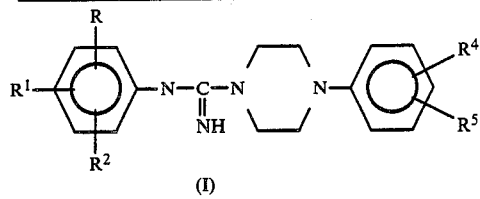

(I)

As outlined in Reaction Scheme I, ammonium thiocynate and benzoyl chloride are reacted in an inert organic solvent such as methyl ethyl ketone, or preferably acetone. An appropriately substituted aniline of formula 1 in an organic solvent such as toluene, xylene, CCl₄, DMF, DMSO or preferably acetone, is added with heating to about 50°–100° C., to give the corresponding thiourea compound of formula 2.

Reaction of the thiourea (formula 2) with methyl iodide in water, ethanol, or preferably acetone, gives the methyl ester of the corresponding carbamidothioic acid (formula 3), which is then condensed with an appropriately substituted 1-phenyl-piperazine of formula 4 to yield the desired compound of Formula 1.

Appropriately substituted anilines of formula 1 are readily commercially available, or can be prepared by standard methods well known in the art. 1-Phenyl-piperazine and its appropriately substituted derivatives are also readily commercially available, or can be prepared by the reaction of an appropriately substituted or unsubstituted aniline with 2,2′-dichlorodiethylamine, as described by K. Brewster in Chim. Ther. 1972, 7(2), 87–91.

B. Compounds of Formula I in which R₃ is not Hydrogen

Compounds of Formula I in which R₃ is a non-hydrogen substituent are prepared as shown in Reaction Scheme II, below:

REACTION SCHEME II

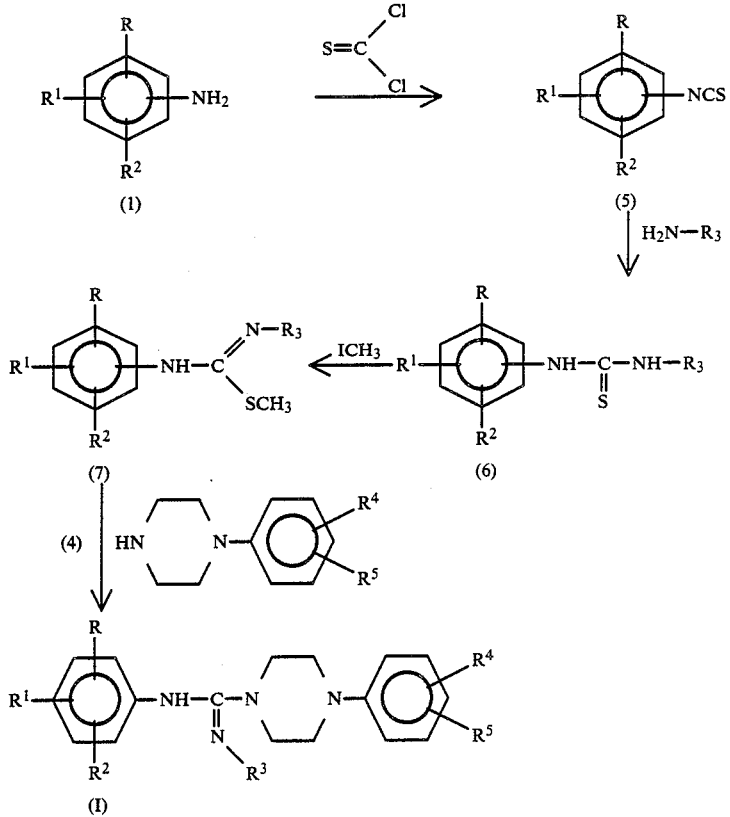

As outlined above, an appropriate optionally substituted aniline of formula 1 is reacted with thiophosgene in a mixture of dichloromethane and water containing potassium carbonate, sodium carbonate, or preferably, calcium carbonate, for a period of about 6 to 18, preferably 12, hours at about 25°–40° C., preferably 25° C., to give the optionally substituted isothiocyanate of formula 5. This procedure is discussed in greater detail by E. Houkanen, et al., *Heterocycle Chem.*, 17. pp. 797–798. (1980).

The isothiocyanate of formula 5 is then reacted with the desired amine, such as methylamine, isopropylamine or isobutylamine, in an organic solvent such as methanol, diethyl ether, petroleum ether, or preferably ethanol. The reaction takes place at about 30° C. to reflux over a period of 0.5–24, preferably 1–8, hours.

The resulting thiourea of formula 6 is then reacted with methyl iodide to give the corresponding carboxamidothioic acid methyl ester of formula 7. The reaction is carried out in a polar organic solvent such as methanol, ethanol, or preferably acetone, at about 40° C. to, preferably, reflux. Alternatively, the reaction takes place in a mixture of water and sodium hydroxide at about 20°-30° C., preferably 25° C., and is followed by extraction with dichloromethane.

The carbamimidothioic acid methyl ester of formula 7 is converted to the corresponding piperazine carboxamindine of Formula I by reaction with an appropriate optionally substituted 1-phenyl-piperazine of formula 4. As discussed above in Section A, appropriately substituted or unsubstituted 1-phenyl-piperazines are readily commercially available, or can be prepared from the corresponding aniline. The conversion of the compound of formula 7 is carried out in a polar, organic solvent such as acetone, methanol, or preferably ethanol, under reflux for a period of about 2 to 24, preferably about 12, hours.

If desired, the compounds of formula I can be converted to corresponding pharmaceutically acceptable acid addition salts. Salts of the compounds of Formula I are prepared by reacting the corresponding free bases with appropriate acids or acid salts at a temperature of between 0° and 100° C. Conversely, free bases can be prepared by reacting corresponding acid addition salts with suitable alkaline agents, such as sodium or potassium hydroxide at 0°-100° C.

Compounds of Formula I wherein any of $R_4$ and $R_5$ are —OH and/or $R_3$ is lower alkyl—OH may be esterified to convert them to the corresponding alkanoyl derivatives. This is accomplished by heating the compound of Formula I with a molar excess of the appropriate carboxylic anhydride or halide in a tertiary amine solvent, such as, for example, pyridine. The temperature is kept at about 20° to 90° C., preferably 15° to 30° C.

Additionally, alkanoyl derivatives of the carboxamidine moiety (compounds of Formula I in which $R^3$

is can be prepared by reacting a compound of Formula I with an appropriate carboxylic anhydride, optionally in the presence of a basic catalyst such as pyridine, using standard reaction conditions.

Isolation and purification of each of the invention compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures could, of course, also be used.

The salt products are also isolated by conventional means. For example, the reaction mixtures may be evaporated to a dryness, and the salts can be further purified by conventional methods.

The compounds of Formula I process useful antiarrythmic activity in humans as well as other mammals. The degree of antiarrhythmic activity of each compound of the invention can be determined by the coronary artery ligation-induced ventricular arrhythmia assay, details of which are provided in Example 21.

Administration of the active compounds and salts and esters described herein can be via any of the accepted modes of administration for systemically active therapeutic medicaments. These methods include oral, parenteral and otherwise systemic, aerosol or topical forms.

Depending on the intended mode of administration, the compositions used may be in the form of solid, semi-solid or liquid dosage forms, such as, for example, tablets, suppositories, pills, capsules, powders, liquids, aerosols, suspensions, or the like, preferably in unit dosage forms suitable for single administration of precise dosages. The compositions will include a conventional pharmaceutical carrier or excipient and an active compound of Formula I or the pharmaceutically acceptable acid addition salts and esters thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Penna., 15th Edition, 1975. The composition or formulation to be administered will, in any event, contain a quantity of the active compound(s) in an amount effective to alleviate the symptoms of the subject being treated.

For the compounds of Formula I, either parenteral, oral or nasal (bronchial) administration is preferred, depending on the nature of the disorder being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

Oral and nasal administration to the lungs can also be effected by aerosol delivery forms. For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with a pharmaceutically acceptable non-toxic carrier. A suitable range of composition would be 0.1%–10% active ingredient, and the balance carrier, preferably 1–2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and palmitic acid; and 0 to 20 wt. percent of a penetrant such as dimethyl sulfoxide or dimethylacetamide.

The amount of active compound administered will of course, be dependent on the subject being treated, the severity of the affliction, the manner of administration and the judgement of the prescribing physician. However, an effective dosage is in the range of 0.5–50 mg/kg/day, preferably about 10 mg/kg/day. For an average 70 kg human, this would amount to 35 mg –3.5 g per day, or preferably about 0.7 g/day.

The following examples serve to illustrate the invention. They should not be construed as narrowing or limiting its scope.

EXAMPLE 1

A.

Preparation of N-[3,5-Dichlorophenyl]thiourea and Related Compounds of Formula 2

To a mixture of 4 liters of acetone and 110 g (1.5 moles) of ammonium thiocyanate are added dropwise 173 g (1.23 moles) of benzoyl chloride. The reaction mixture is then heated for a further 15 minutes. Next, 200 g (1.23 moles) of 3,5-dichlorophenyl aniline dissolved in 200 ml of acetone are added. The mixture is then heated for a further 30 minutes, cooled and poured into 4 liters of water. The precipitate is collected and rinsed with 1 liter of water. The crystals are mixed with 2 liters of water containing 50 g of sodium hydroxide. The mixture is heated for 30 minutes and then cooled. The precipitate is collected to give 238 g (88%) of N-[3,5-dichlorophenyl]thiourea, m.p. 180° C.

B.

In a similar manner but replacing the 3,5-dichlorophenyl aniline with other appropriately substituted anilines of formula 1, the following compounds of formula 2 were prepared:
N-[2,3-dimethylphenyl]thiourea;
N-[4-methylphenyl]thiourea;
N-[2-chlorophenyl]thiourea;
N-[2,5-dimethylphenyl]thiourea;
N-[3,5-dimethylphenyl]thiourea;
N-[4-fluoro-3-trifluromethylphenyl]thiourea;
N-[2-chloro-4-nitrophenyl]thiourea;
N-[4-ethylphenyl]thiourea;
N-[4-n-butylphenyl]thiourea;
N-[3-chlorophenyl]thiourea;
N-[4-methoxyphenyl]thiourea;

C.

Similarly, but starting instead with other appropriately substituted anilines of formula 1, the following representative compounds of formula 2 are prepared:

N-[3,5-dichlorophenyl]thiourea
N-[2,3,4-trifluorophenyl]thiourea;
N-[2-trifluoromethylphenyl]thiourea;
N-[3-methyl-5-chlorophenyl]thiourea;
N-[3,5-dinitrophenyl]thiourea;
N-[3,5-dibromophenyl]thiourea and
N-[3,4-dimethoxyphenyl]thiourea.

EXAMPLE 2

A.

Preparation of N-[3,4-dichlorophenyl] carbamimidothioic acid, methyl ester hydroiodide and Related Compounds of Formula 3

To 110 g (0.45 mole) of N-[3,5-dichlorophenyl]thiourea in 500 ml of acetone were added dropwise, under reflux, 64.2 g of methyl iodide. After this addition, the mixture was refluxed for a further 2 hours and was then left for 8 hours at room temperature. The precipitate was collected and rinsed with ether to give 95 g (45.6%) of N-[3,4-dichlorophenyl] carbamimidothioic acid, methyl ester, hydroiodide.

B.

In a similar manner, but substituting for the N-[3,5-dichlorophenyl]thiourea, other compounds of formula 2, prepared as described in Example I, the following compounds of formula 3 were prepared:

N-[2,3-dimethylphenyl] carbamimidothioic acid, methyl ester, hydroiodide;
N-[4-methylphenyl] carbamimidothioic acid, methyl ester, hydroiodide;
N-[2-chlorophenyl] carbamimidothioic acid, methyl ester, hydroiodide;
N-[2,5-dimethylphenyl] carbamimidothioic acid, methyl ester, hydroiodide;
N-[3,5-dimethylphenyl] carbamimidothioic acid, methyl ester, hydroiodide;
N-[4-fluoro-3-trifluoromethyl] carbamimidothioic acid, methyl ester, hydroiodide;
N-[2-chloro-4-nitrophenyl] carbamimidothioic acid, methyl ester, hydroiodide;
N-[4-ethylphenyl] carbamimidothioic acid, methyl ester, hydroiodide;
N-[4-n-butylphenyl] carbamimidothioic acid, methyl ester, hydroiodide;
N-[3-chlorophenyl] carbamimidothioic acid, methyl ester, hydroiodide; and
N-[4-methoxyphenyl] carbamimidothioic acid, methyl ester, hydroiodide.

C.

Similarily, but using other suitable compounds of formula 2, prepared according to the method described in Example 1 A–C., the following representative compounds of formula 3 are prepared:

N-[3,5-dichlorophenyl] carbamimidothioic acid, methyl ester, hydroiodide;
N-[2,3,4-trifluorophenyl] carbamimidothioic acid, methyl ester, hydroiodide;
N-[2-trifluoromethylphenyl] carbamimidothioic acid, methyl ester, hydroiodide;
N-[3-methyl-5-chlorophenyl] carbamimidothioic acid, methyl ester, hydroiodide;
N-[3,5-dinitrophenyl] carbamimidothioic acid, methyl ester, hydroiodide;
N-[3,5-dibromophenyl] carbamimidothioic acid, methyl ester, hydroiodide; and
N-[3,4-dimethoxyphenyl] carbamimidothioic acid, methyl ester, hydroiodide.

EXAMPLE 3

A.

Preparation of 1-Piperazinecarboxamidine-N-[3,5-dichlorophenyl]-4-[2-methoxyphenyl], dimethane sulfonate, and Related compounds of Formula I A solution of 19 g of N-[3,5-dichlorophenyl] carbamimidothioic acid, methyl ester and 15 g (0.078 mole) of 2-methoxyphenyl piperazine in 250 ml of ethanol was heated for 8 hours under reflux. The mixture was evaporated and the residue triturated in a mixture of acetone and isopropyl ether. The precipitate was collected, dried and dissolved in 200 ml of acetone containing 7.5 g of methane sulfonic acid. The crystals were collected and dried to give 25 g (56%) of 1-piperazinecarboxamidine-N-[3,5-dichlorophenyl]-4-[2-methoxyphenyl], dimethane sulfonate, m.p. 154° C.

B.

Similarly, but replacing the N-[3,5-dichlorophenyl]-4-[2-methoxyphenyl]carbamimidothioic acid with other compounds of formula 3, prepared as described in Example 2, and substituting where appropriate other 1-phenyl-piperazines of formula 4, the following compounds of Formula 1 were prepared:

1-piperazinecarboxamidine-N-[3,5-dichlorophenyl]-4-[2-methoxyphenyl-4-hydroxyphenyl], dihydrochloride, m.p. 230° C.;
1-piperazinecarboxamidine-N-[3,5-dichlorophenyl]-4-[2-methoxyphenyl], dihydrochloride, m.p. 202° C.;
1-piperazinecarboxamidine-N-[2,3-dimethylphenyl]-4-[2-methoxyphenyl], dihydrochloride, m.p. 215° C.;
1-piperazinecarboxamidine-N-[4-methylphenyl]-4-[2-methoxyphenyl], dihydrochloride, m.p. 150° C.;
1-piperazinecarboxamidine-N-[2-chlorophenyl]-4-[2-methoxyphenyl], dihydrochloride, m.p. 208° C.;
1-piperazinecarboxamidine-N-[2,5-dimethylphenyl]-4-[2-methoxyphenyl]dihydrochloride, m.p. 191° C.;
1-piperazinecarboxamidine-N-[3,5-dimethylphenyl]-4-[2-methoxyphenyl], fumarate, m.p. 164° C.;
1-piperazinecarboxamidine-N-[4-fluoro-3-trifluoromethylphenyl]-4-[2-methoxyphenyl], dihydrochloride, m.p. 240° C.;
1-piperazinecarboxamidine-N-[2-chloro-4-nitrophenyl-4-[2-methoxyphenyl], dihydrochloride, m.p. 240° C.;
1-piperazinecarboxamidine-N-[4-ethylphenyl]-4-[2-methoxyphenyl], dihydrochloride, m.p. 160° C.;
1-piperazinecarboxamidine-N-[4-butylphenyl]-4-[2-methoxyphenyl], fumarate, m.p. 192° C.;
1-piperazinecarboxamidine-N-[3,5-dichlorophenyl]-4-[2-chlorophenyl], hydrochloride, m.p. 485° C.;
1-piperazinecarboxamidine-N-[3,5-dichlorophenyl]-4-[4-fluorophenyl], hydrochloride, m.p. 140° C.;
1-piperazinecarboxamidine-N-[3,5-dichlorophenyl]-4-[3-trifluorophenyl], hydrochloride, m.p. 175° C.;
1-piperazinecarboxamidine-N-[4-methoxyphenyl]-4-[2-methoxyphenyl], dihydrochloride, m.p. 210° C.;

1-piperazinecarboxamidine-N-[3,4-dichlorophenyl]-4-[2-methoxyphenyl], dihydrochloride, m.p. 201° C.;

1-piperazinecarboxamidine-N-[4-chlorophenyl]-4-[2-methoxyphenyl], dihydrochloride, m.p. 200° C.;

1-piperazinecarboxamidine-N-[3,5-dichlorophenyl]-4-[2-methoxy-5-hydroxyphenyl], dihydrochloride, m.p. 232° C.;

1-piperazinecarboxamidine-N-[3,5-dichlorophenyl]-4-[2,4-dimethoxyphenyl], dihydrochloride, m.p. 230° C.; and 1-piperazinecarboxamidine-N-[3,5-dichlorophenyl]-4-[2-hydroxyphenyl], dihydrochloride, m.p. 230° C.

EXAMPLE 4

A.

Preparation of N-[3,5-Dichlorophenyl]-N'-[2-methylpropyl]-2-thiourea, and Related Compounds of Formula 6

To a solution of 20.4 g (0.279 mole) of isobutylamine in 300 ml of ethanol were added dropwise, under reflux, 57 g (0.279 mole) of 3,4-dichlorophenylisothiocyanate. After this addition, refluxing was continued for a further 2 hours. The reaction mixture was then cooled and the precipitate collected to give 54 g (70%) of N-[3,5-dichlorophenyl]-N'-[2-methylpropyl]-2-thiourea, m.p. 144° C.

B.

In a similar manner, but replacing, where appropriate, the isobutylamine and the 3,4-dichlorophenylisothiocyante with other appropriate amines and optionally substituted compounds of formula 5, the following compounds of formula 6 were prepared:

N-[3,4-dichlorophenyl]-N'-[methyl]-2-thiourea;
N-[3,5-dichlorophenyl]-N'-[methyl]-2-thiourea;
N-[phenyl]-N'-[isobutyl]-2-thiourea;
N-[3,5-dichlorophenyl]-N'-[n-butyl]-2-thiourea;
N-[3,4-dichlorophenyl]-N'-[isobutyl]-2-thiourea;
N-[3,4-dichlorophenyl]-N'-[3-hydroxypropyl]-2-thiourea;
N-[phenyl]-N'-[2-propenyl]-2-thiourea;
N-[phenyl]-N'-[3-hydroxypropyl]-2-thiourea;
N-[3,4-dichlorophenyl]-N'-[2-propenyl]-2-thiorurea; and
N-[3,5-dichlorophenyl]-N'-[2-hydroxypropyl]-2-thiourea.

C.

Similarily, but starting instead with other amines and optionally substituted compounds of formula 5 where appropriate, the following compounds of formula 6 are prepared:

N-[3,5-dichlorophenyl]-N'-[2-propenyl]-2-thiourea;
N-[2,3,4-trifluorophenyl]-N'-[ethyl]-2-thiourea;
N-[2-trifluoromethylphenyl]-N'-[isobutyl]-2-thiourea
N-[3-methyl-5-chlorophenyl]-N'-[2-hydroxypropyl]-2-thiourea;
N-[3,5-dinitrophenyl]-N'-[n-butyl]-2-thiourea;
N-[3,5-dibromophenyl]-N'-[isobutyl]-2-thiourea; and
N-[3,4-dimethoxyphenyl]-N'-[2-propenyl]-2-thiourea.

EXAMPLE 5

A.

Preparation of N-[3,5-Dichlorophenyl]-N'-[2-methylpropyl]carbamimidothioic acid, methyl ester, hydroiodide, and Related Compounds of Formula 7.

A solution of 53 g of N-[3,5-dichlorophenyl]-N'-[2-methylpropyl]thiourea in 200 ml of acetone was heated under reflux. A total of 16 ml of methyl iodide was added dropwise, heating is continued for a further 3 hours after this addition. The reaction mixture was then cooled and the precipitate collected to give 50 g (55.5%) of N-[3,5-dichlorophenyl]-N'-[2-methylpropyl]-carbamimidothioic acid, methyl ester, hydroiodide, m.p. 150° C. Concentration of the mother liquors and recrystallization in ethanol/isopropyl ether afforded a further 20 g of the product. Total yield: 77%.

B.

In like manner, but starting with other appropriately substituted compounds of formula 6, prepared in accordance with the method described in Example 4, the following compounds of formula 7 were prepared:

N-[3,4-dichlorophenyl]-N'-[methyl]carbamimidothioic acid, methyl ester, hydroiodide;
N-[3,5-dichlorophenyl]-N'-[methyl]carbamimidothioic acid, methyl ester, hydroiodide;
N-[phenyl]-N'-[isobutyl]carbamimidothioic acid, methyl ester, hydroiodide;
N-[3,5-dichlorophenyl]-N'-[n-butyl]carbamimidothic acid, methyl ester, hydroiodide;
N-[3,4-dichlorophenyl]-N'-[isobutyl]carbamimidothioic acid, methyl ester, hydroiodide;
N-[3,4-dichlorophenyl]-N'-[3-hydroxypropyl]carbamimidothioic acid, methyl ester, hydroiodide;
N-[phenyl]-N'-[2-propenyl]carbamimidothioic acid, methyl ester, hydroiodide;
N-[phenyl]-N'-[3-hydroxypropyl]carbamimidothioic acid, methyl ester, hydroiodide;
N-[3,4-dichlorophenyl]-N'-[2-propenyl]carbamimidothioic acid, methyl ester, hydroiodide; and
N-[3,5-dichlorophenyl]-N'-[2-hydroxypropyl]carbamimidothioic acid, methyl ester, hydroiodide.

C.

Similarily, but starting with other suitable compounds of formula 6, prepared according at the method described in Example 4.C., the following compounds of formula 7 are prepared:

N-[3,5-dichlorophenyl]-N'-[2-propenyl]carbamimidothioic acid, methyl ester, hydroiodide;
N-[2,3,4-trifluorophenyl]-N'-[ethyl]carbamimidothioic acid, methyl ester, hydroiodide;
N-[2-trifluoromethylphenyl]-N'-[isobutyl]carbamimidothioic acid, methyl ester, hydroiodide;
N-[3-methyl-5-chlorophenyl]-N'-[2-hydroxypropyl]carbamimidothioic acid, methyl ester, hydroiodide;
N-[3,5-dinitrophenyl]-N'-[n-butyl]carbamimidothioic acid, methyl ester, hydroiodide;
N-[3,5-dibromophenyl]-N'-[isobutyl]carbamimidothioic acid, methyl ester, hydroiodide;
N-[3,4-dimethoxyphenyl]-N'-[2-propenyl]carbamimidothioic acid, methyl ester hydroiodide;

EXAMPLE 6

A.

Preparation of 1-Piperazinecarboxamidine N-[3,5-dichlorophenyl]-N'-[2-methylpropyl]-4-[2-methoxyphenyl], dihydrochloride, and Related Compounds of Formula I 13.5 g of N-[3,5-dichlorophenyl]-N'-[2-methylpropyl]carbamimidothioic acid, methyl ester and 9.35 g of 1-[2-methoxyphenyl]piperazine in 200 ml of ethanol were heated under reflux for 12 hours. On cooling of the solution, the free base separated and was then purified by crystallization from ethanol (m.p. 110° C.). Alternatively, addition of hydrochloric acid to the reaction medium gives, by cooling, 14.5 g (72%) of a white crystalline product which melts at 210° C.

B.

In like manner, but replacing the N-[3,5-dichlorophenyl]-N'-[2-methylpropyl]carbamimidothioic acid, methyl ester, and the 1-[2-methoxyphenyl]piperazine with other compounds of formulas 7 and 4, respectively, as needed, the following compounds of formula I were prepared, and converted to the indicated acid addition salt:

1-piperazinecarboxamidine-N-[3,4-dichlorophenyl]-N'-[methyl]-4-[2-methoxyphenyl]dihydrochloride, m.p. 170° C.;

1-piperazinecarboxamidine-N-[3,5-dichlorophenyl]-N'-[methyl]-4-[2-methoxyphenyl], dihydrochloride, m.p. 175° C.;

1-piperazinecarboxamidine-N-[phenyl]-N'-[isobutyl]-4-[2-methoxyphenyl], fumarate, m.p. 195° C.;

1-piperazine carboxamidine-N-[3,5-dichlorophenyl-N'-[isobutyl]-4-[2-methoxyphenyl], dihydrochloride, m.p. 210° C.;

1-piperazinecarboxamidine-N-[3,5-dichlorophenyl]-N'-[n-butyl]-4-[2-methoxyphenyl], dihydrochloride, m.p. 184° C.;

1-piperazinecarboxamidine-N-[3,4-dichlorophenyl]-N'-[isobutyl]-4-[2-methoxyphenyl], dihydrochloride, m.p. 210° C.;

1-piperazinecarboxamidine-N-[2,6-dimethylphenyl]-N'-[isobutyl]-4-[2-methoxyphenyl], fumarate, m.p. 220° C.;

1-piperazinecarboxamidine-N-[3,4-dichlorophenyl]-N'-[3-hydroxypropyl]-2-[methoxyphenyl], hydrochloride, m.p. 215° C.;

1-piperazinecarboxamidine-N-[phenyl]-N'-[2-propenyl]-4-[2-methoxyphenyl], hydrochloride, m.p. 195° C.;

1-piperazinecarboxamidine-N-[phyenyl]-N'-[3-hydroxypropyl]-4-[2-methoxyphenyl], hydrochloride, m.p. 200° C.;

1-piperazinecarboxamidine-N-[3,4-dichlorophenyl]-N'-[2-propenyl]-4-[2-methoxyphenyl], hydrochloride, m.p. 180° C.; and 1-piperazinecarboxamidine N-[3,5-dichlorophenyl]-N'(2-hydroxypropyl)-4-[2-methoxyphenyl], hydrochloride, m.p. 225° C.

C.

Similarly, but starting with other appropriate compounds of formulas 3 and 7, obtained as described in Examples 2 and 5, and substituting as desired other suitable compounds of formula 4, the following compounds of Formula I are prepared, and if desired, are converted to their pharmaceutically acceptable acid addition salts and esters:

N-[3,5-dichlorophenyl]-N'-[2-propenyl]]-4-[phenyl]-piperazinecarboxamidine;

N-[2,3,4-trifluorophenyl]-N'-[ethyl]-4-[2-bromophenyl]-1-piperazinecarboxamidine;

N-[2-trifluoromethylphenyl]-N'-[isobutyl]-4-[2-methoxy-4-hydroxyphenyl]-1-piperazinecarboxamidine;

N-[3-methyl-5-chlorophenyl]-N'-[2-hydroxypropyl]-4-[2-methoxyphenyl]-1-piperazinecarboxamidine;

N-[3,5-dinitrophenyl]-N'-[n-butyl]-4-[2,6-dimethylphenyl]-1-piperazinecarboxamidine;

N-[3,5-dibromophenyl]-N'-[isobutyl]-4-[2-methoxy-4-hydroxyphenyl]-1-piperazinecarboxamidine;

N-[3,4-dimethoxyphenyl]-N'-[2-propenyl]-4-[4-fluorophenyl]-1-piperazinecarboxamidine;

N-[3,5-dichlorophenyl]-4-[phenyl]-1-piperazinecarboxamidine;

N-[2,3,4-trifluorophenyl]-4-(2-bromophenyl)-1-piperazinecarboxamidine;

N-[2-trifluoromethylphenyl]-4-[2-methoxy-4-hydroxyphenyl]-1-piperazinecarboxamidine;

N-[3-methyl-5-chlorophenyl]-4-[2-methoxyphenyl]-1-piperazinecarboxamidine;

N-[3,5-dinitrophenyl]-4-[2,6-dimethylphenyl]-1-piperazinecarboxamidine;

N-[3,5-dibromophenyl]-4-[2-methoxy-4-hydroxyphenyl]-1-piperazinecarboxamidine; and N-[3,4-dimethoxyphenyl]-4-[4-fluorophenyl]-1-piperazinecarboxamidine;

EXAMPLE 7

Conversion of free base to salt

Excess 3% hydrodgen chloride in methanol is added to a solution of 1.0 g. N-[3,5-dichlorophenyl]-4-[2-methoxyphenyl]-1-piperazinecarboxamidine in 20 ml methanol. Diethyl ether is added until precipitation is complete. The product dihydrochloride is filtered, washed with ether, air dried and recrystallized.

In similar manner, other compounds of Formula I in free base form may be converted to acid addition salts by treatment with the appropriate acid, for example, hydrochloric acid, hydrobromic acid, sulfuric acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, lactic acid and the like.

EXAMPLE 8

Conversion of salt to free acid 1.0 g of 1-piperazinecarboxamidine N-[3,5-dichlorophenyl]-4-[2-methoxyphenyl], dihydrochloride suspended in 50 ml of ether is stirred with excess dilute aqueous potassium carbonate solution until the salt is completely dissolved. The organic layer is then separated, washed twice with water, dried over magnesium sulfate and evaporated to yield N-[3,5-dichlorophenyl]-4-[2-methoxyphenyl]-1-piperazinecarboxamidine, as the free base.

EXAMPLE 9

Direct interchange of acid addition salts 5 g of 1-piperazinecarboxamidine N-[3,5-dichlorophenyl]-4-[2-methoxyphenyl], dilactate (m.p. 168° C.)

are poured into 250 ml of distilled water. The solution is added dropwise to the stoichiometric quantity of methane sulfonic acid under stirring. The dimethane sulfonate separates. Crystallization of the solid from ethanol/water (60/40-v/v) yields 3.8 g of purified 1-piperazinecarboxamidine N-[3,5-dichlorophenyl]-4-[2-methoxy-4-hydroxyphenyl], dimethane sulfonate, m.p. 270° C.

EXAMPLE 10

Conversion of alcohol to ester

A.

A solution of 0.10 mole of N-[3,5-dichlorophenyl]-N'-methyl-4-[2-methoxy-4-hydroxy phenyl]-1-piperazine-carboxamidine, 0.12 mole of pyridine and 0.12 mole of acetic anhydride in 250 ml of dichloromethane was stirred 12 hours at room temperature and poured into 2 L water. The organic phase was separated, washed with cold water, dried on sodium sulfate and evaporated. The residue (oil) was purified by flash chromatography on silica gel (200 mesh) using ethylacetate (60)/methanol (40) as eluant. The first 250 ml of eluant were collected and evaporated, and the residue further purified by recrystallization, to give N-[3,5-dichlorophenyl]-N'-methyl-4-[2-methoxy-4-acetyloxy-phenyl]-1-piperazine-carboxamidine, m.p. 144° C.

B.

In a manner similar to that describe in part A of this Example, other esters such as the corresponding n-propionyloxy, isobutyryloxy, n-oxy, and n-valeryl derivatives are prepared from compounds of Formula I.

EXAMPLE 11

Conversion of carboxamidine to an alkanoyl derivative

A.

A suspension of 4 g of 1-piperazinecarboxamidine-N-[3,5-dichlorophenyl]-4-[2-methoxyphenyl], dihydrochloride (0.01M) in 200 ml of dichloromethane was combined with 0.03M of pyridine under stirring. When dissolution was completed, 1.5 g (0.011 M) of acetic anhydride were added and the mixture was heated at about 40° C. for 1 hour and then poured into 1 L water. The organic phase was separated, washed, dried, evaporated, and the residue recrystallized from isopropyl ether to give N-[3,5-dichlorophenyl]-N'-acetyl-4-[2-methoxyphenyl]-1-piperazinecarboxamidine.

B.

In a similar manner to that described in part A of this Example, other corresponding alkanoyl derivatives such as N-propionyl, isobutyryl, n-valeryl, heptanoyl and 4-ethylhexanoyl are prepared from the amidine moiety of compounds of Formula I.

EXAMPLE 12

Simultaneous conversion of alcohol to ester and carboxamidine to alkanoyl derivative

A.

A mixture of 10 g of 1-piperazinecarboxamidine-N-[3,5-dichlorophenyl]-4-[2-methoxy-4-hydroxy-phenyl], dihydrochloride and 250 ml of acetic anhydride is heated for 12 hours under reflux. The mixture is evaporated and the residue then crystallized from aqueous ethanol (60%) to give 9 g of 1-piperazinecarboxamidine-N-[3,5-dichlorophenyl]-N'-acetyl-4-[methoxy-4-acetyloxy-phenyl], dihydrochloride, m.p. 194° C.

B.

In a similar manner, other compounds of Formula I bearing ring alcohol substitution are converted to their corresponding ester and alkanoyl derivatives, such as those described in Examples 10 and 11.

In Examples 13–20 the active ingredient is 1-piperazinecarboxamidine N-[3,5-dichlorophenyl]-4-[2-methoxyphenyl]dihydrochloride; however, any of the compounds of this invention can be substituted in its place.

EXAMPLE 13

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thorougly mixed and pressed into single scored tablets.

EXAMPLE 14

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 15

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 16

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 17

| Ingredients | Quantity per tablet, mgs. |
| --- | --- |
| Active ingredient | 150 |

-continued

| Ingredients | Quantity per tablet, mgs. |
|---|---|
| lactose | 92 |

The above ingredients are mixed and introduced into a hard-shell gelatin capsule.

EXAMPLE 18

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

A 1.0% solution may be raised to a pH of 5 to 6 without precipitation.

EXAMPLE 19

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 20

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 21

Coronary Artery Ligation-Induced Ventricular Arrhythmia Assay

Mongrel dogs (approx 10 kg) were anaesthetised with pentobarbone 35 mg.kg$^{-1}$ i.v. The anterior descending branch of the left coronary artery was dissected free in the area of the left atrial appendage. A 2-stage ligation was applied according to the model of Harris (Circulation 1, 1318, 1950). Lead II ECG measurements were recorded 24 hours later for a control period of one hour. Only dogs demonstrating more than 90% beats of ventricular origin were used. Test compounds (or placebo) were subsequently administered orally or intravenously and ECGs were monitored for up to 6 hours. The effects of the test compound on coronary artery ligation-induced arrhythmia are expressed as % inhibition of abnormal ECG complexes from samples analyzed over 1 and 6 hour periods.

In this manner, relative potencies for protection against arrhythmia are compared for single and cumulative oral doses. Relative activity is calculated from the area under the curve for each compound.

What is claimed:

1. A compound of the formula:

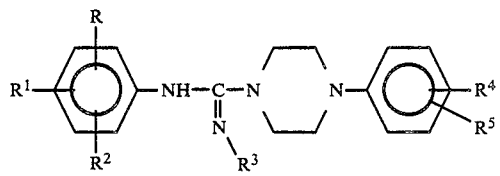

in which:

R, R$^1$ and R$^2$ are each independently hydrogen, halo, lower alkyl, lower alkoxy, —CF$_3$ or —NO$_2$, with the proviso that R is hydrogen when both R$^1$ and R$^2$ are iodo or —NO$_2$;

R$^3$ is hydrogen, lower alkyl, lower alkyl—OH,

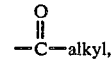

or lower alkenyl; and

R$^4$ and R$^5$ are each independently hydrogen, halo, lower alkoxy, —OH, —CH$_3$ or

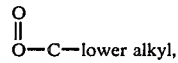

and the pharmaceutically acceptable acid addition salts and esters thereof.

2. A compound of claim 1 in which R is hydrogen, and the pharmaceutically acceptable acid addition salts and esters thereof.

3. A compound of claim 2 wherein R$^4$ and R$^5$ are each independently hydrogen, —OH or lower alkoxy, and at least one of R$^4$ and R$^5$ is not hydrogen, and the pharmaceutically acceptable acid addition salts and esters thereof.

4. A compound of claim 3 in which R$^4$ and R$^5$ are each independently hydrogen, —OH or lower alkoxy in the 2- and 4- positions of the phenyl ring, and R$^3$ is hydrogen, lower alkyl or lower alkyl—OH, and the pharmaceutically acceptable acid addition salts and esters thereof.

5. The compound of claim 4 in which R$^1$ and R$^2$ are both hydrogen, R$^3$ is hydroxypropyl, R$^4$ is methoxy in the 2- position, and R$^5$ is hydrogen, namely N-[phenyl]-N'-[3-hydroxypropyl-4-2-methoxyphenyl]-1-piperazinecarboxamidine, and the pharmaceutically acceptable acid addition salts and esters thereof.

6. The compound of claim 4 in which R$^1$ and R$^2$ are hydrogen, R$^3$ is isobutyl, R$^4$ is methoxy in the 2-position, and R$^5$ is hydrogen, namely N-[phenyl]-N'[isobutyl]-4-[2-methoxyphenyl]-1-piperazinecarboxamidine and the pharmaceutically acceptable acid addition salts thereof.

7. The compound of claim 4 in which $R^1$ and $R^2$ are each hydrogen, $R^3$ is n-butyl, $R^4$ is methoxy in the 2- position, and $R^5$ is hydrogen, namely N-[phenyl]-N'-[n-butyl]-4-[2-methoxyphenyl]-piperazinecarboxamidine, and the pharmaceutically acceptable acid addition salts thereof.

8. A compound of claim 2 in which $R^1$ and $R^2$ are each independently hydrogen, lower alkyl, or halo and at least one of $R^1$ and $R^2$ is not hydrogen, and the pharmaceutically acceptable acid addition salts and esters thereof.

9. The compound of claim 8 in which $R^1$ and $R^2$ are each chloro in the 3- and 5- positions, $R^3$ is hydrogen, $R^4$ is fluoro in the 4- position, and $R^5$ is hydrogen, namely N-[3,5-dichlorophenyl]-4-[4-fluorophenyl]-1-piperazinecarboxamidine, and the pharmaceutically acceptable acid addition salts thereof.

10. The compound of claim 8 in which $R^1$ and $R^2$ are each chloro in the 3- and 5- positions, $R^3$ is hydrogen, $R^4$ is trifluoromethyl in the 3- position, and $R^5$ is hydrogen, namely N-[3,5-dichlorophenyl]-4-[3-trifluoromethylphenyl]-1-piperazinecarboxamidine, and the pharmaceutically acceptable acid addition salts thereof.

11. A compound of claim 8 in which $R^4$ and $R^5$ are each independently hydrogen, —OH or lower alkoxy, and at least one of $R^4$ and $R^5$ is not hydrogen, and the pharmaceutically acceptable acid addition salts and esters thereof.

12. A compound of claim 11 in which $R^4$ and $R^5$ are each independently hydrogen, —OH or lower alkoxy in the 2- and 4- positions, and the pharmaceutically acceptable acid addition salts and esters thereof.

13. A compound of claim 12 in which $R^3$ is hydrogen, lower alkyl or lower alkyl—OH, and the pharmaceutically acceptable acid addition salts and esters thereof.

14. A compound of claim 13 wherein $R^1$ and $R^2$ are each independently hydrogen, methyl or chloro, and the pharmaceutically acceptable acid addition salts and esters thereof.

15. The compound of claim 14 in which $R^1$ and $R^2$ are each chloro in the 3- and 5- positions, $R^3$ is hydrogen, and $R^4$ and $R^5$ are methoxy and hydroxy, respectively, namely N-[3,5-dichlorophenyl]-4-[2-methoxy-4-hydroxyphenyl]-1-piperazinecarboxamidine and the pharmaceutically acceptable acid addition salts and esters thereof.

16. The compound of claim 14 in which $R^1$ and $R^2$ are each chloro in the 3- and 5- positions, $R^3$ is hydrogen, $R^4$ is methoxy in the 2- position and $4^5$ is hydrogen, namely N-[3,5-dichlorophenyl]-4-[2-methoxyphenyl]-1-piperazinecarboxamidine, and the pharmaceutically acceptable acid addition salts thereof.

17. The compound of claim 14 in which $R^1$ and $R^2$ are each chloro in the 3- and 4- positions, $R^3$ is hydrogen, $R^4$ is methoxy in the 2- position, and $R^5$ is hydrogen, namely N-[3,4-dichlorophenyl]-4-[2-methoxyphenyl]-1-piperazinecarboxamidine, and the pharmaceutically acceptable acid addition salts thereof.

18. The compound of claim 14 in which $R^1$ and $R^2$ are each chloro in the 3- and 4- positions, $R^3$ is isobutyl, $R^4$ is methoxy in the 2- position, and $R^5$ is hydrogen, namely 1-N-[3,4-dichlorophenyl]-N'-4-1-piperazinecarboxamidine, and the pharmaceutically acceptable acid addition salts thereof.

19. A pharmaceutical composition for use in treating arrhythmia in mammals which composition comprises a therapeutically effective amount of a compound of claim 1 in admixture with at least one pharmaceutically acceptable excipient.

20. A method of treating arrhythmia in mammals which comprises administering to a mammal in need of such treatment a therapeutic amount of a compound of claim 1 or a pharmaceutically acceptable acid addition salt or ester thereof.

* * * * *